(12) United States Patent
Wang et al.

(10) Patent No.: US 12,733,937 B2
(45) Date of Patent: Sep. 15, 2026

(54) IMPLANTABLE MEDICAL DEVICE ADAPTABLE TO IRREGULAR ANATOMY

(71) Applicant: BOSTON SCIENTIFIC SCIMED, INC., Maple Grove, MN (US)

(72) Inventors: Jerry Wang, Edina, MN (US); Joshua Mark Inouye, Brooklyn Park, MN (US); James M. Anderson, Corcoran, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 305 days.

(21) Appl. No.: 18/459,770

(22) Filed: Sep. 1, 2023

(65) Prior Publication Data

US 2024/0074763 A1 Mar. 7, 2024

Related U.S. Application Data

(60) Provisional application No. 63/403,476, filed on Sep. 2, 2022.

(51) Int. Cl.
*A61B 17/12* (2006.01)
*A61B 17/00* (2006.01)

(52) U.S. Cl.
CPC .... *A61B 17/12122* (2013.01); *A61B 17/0057* (2013.01); *A61B 2017/00575* (2013.01)

(58) Field of Classification Search
CPC .......... A61B 17/12122; A61B 17/0057; A61B 17/12177; A61B 17/12172
See application file for complete search history.

(56) References Cited

U.S. PATENT DOCUMENTS 9,211,124 B2 12/2015 Campbell et al.
2001/0037129 A1 11/2001 Thill
2006/0015136 A1* 1/2006 Besselink ................ A61F 2/01 606/200
2012/0172927 A1* 7/2012 Campbell ........ A61B 17/12172 606/213
2017/0181751 A1 6/2017 Larsen et al.
(Continued)

FOREIGN PATENT DOCUMENTS

CN 107303191 B 10/2020
CN 107233116 B 3/2021
(Continued)

OTHER PUBLICATIONS

International Search Report and Written Opinion dated Dec. 19, 2023 for International Application No. PCT/US2023/073281.
(Continued)

*Primary Examiner* — Brian T Gedeon
(74) *Attorney, Agent, or Firm* — Seager, Tufte & Wickhem LLP

(57) ABSTRACT

An implantable medical device such as but not limited to a left atrial appendage closure (LAAC) device includes an expandable frame that is movable between a collapsed configuration for delivery and an expanded configuration for deployment. The expandable frame may include a plurality of frame members that are biased into the expanded configuration. The expandable frame may include a biasing member. The LAAC device includes a membrane or covering that spans across an end of the expandable frame.

14 Claims, 16 Drawing Sheets

(56) References Cited

U.S. PATENT DOCUMENTS

| | | | |
|---|---|---|---|
| 2019/0110880 A1 | 4/2019 | Fox et al. | |
| 2019/0209179 A1 | 7/2019 | Subramaniam et al. | |
| 2020/0205840 A1 | 7/2020 | Adawi et al. | |
| 2020/0305889 A1* | 10/2020 | Kaplan ............ | A61B 17/12181 |

FOREIGN PATENT DOCUMENTS

| | | |
|---|---|---|
| WO | 2021059273 A2 | 4/2021 |
| WO | 2022010931 A1 | 1/2022 |

OTHER PUBLICATIONS

Invention Disclosure Submission Form, ID 22-D0367, 21 pages, Received Jul. 12, 2022.

* cited by examiner 90a
90
92
92b
92a
90b
96
94
88

86

98
102a
102
100
102b
104
108
106
102a 98
102
100
104
108
106

132
134
132

138
136
138

132
130
132

164
168
166
168

164
168
166
168

164
168
166
168
10

IMPLANTABLE MEDICAL DEVICE ADAPTABLE TO IRREGULAR ANATOMY

CROSS-REFERENCE TO RELATED APPLICATIONS

This application claims the benefit of priority of U.S. Provisional Application No. 63/403,476 filed Sep. 2, 2022, the entire disclosure of which is hereby incorporated by reference.

TECHNICAL FIELD

The disclosure relates generally to medical devices and more particularly to medical devices that are adapted for use in percutaneous medical procedures including implantation into the left atrial appendage (LAA) of a heart.

BACKGROUND

The left atrial appendage is a small organ attached to the left atrium of the heart. During normal heart function, as the left atrium constricts and forces blood into the left ventricle, the left atrial appendage constricts and forces blood into the left atrium. The ability of the left atrial appendage to contract assists with improved filling of the left ventricle, thereby playing a role in maintaining cardiac output. However, in patients suffering from atrial fibrillation, the left atrial appendage may not properly contract or empty, causing stagnant blood to pool within its interior, which can lead to the undesirable formation of thrombi within the left atrial appendage.

Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation originate in the left atrial appendage. As a treatment, medical devices have been developed which are deployed to close off the left atrial appendage. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example may be found in an implantable medical device that includes an expandable frame defining a profile of the implantable medical device, the expandable frame moveable between a collapsed configuration for delivery and an expanded configuration for deployment. The expandable frame includes a plurality of frame members each having a proximal end and a distal end, a securement member that is adapted to secure the plurality of frame members and to allow the expandable frame to move between the collapsed configuration and the expanded configuration, and a covering extending over the proximal end of at least some of the plurality of frame members.

Alternatively or additionally, at least some of the plurality of frame members may be adapted to bend relative to the securement member when moving between the collapsed configuration and the expanded configuration.

Alternatively or additionally, at least some of the plurality of frame members may be adapted to pivot relative to the securement member when moving between the collapsed configuration and the expanded configuration.

Alternatively or additionally, the plurality of frame members may include a plurality of sealing frame members over which the covering extends, and a plurality of anchoring frame members that are adapted to anchor the implantable medical device in place.

Alternatively or additionally, the plurality of sealing frame members may pivot in a first direction when moving from the collapsed configuration to the expanded configuration and the plurality of anchoring frame members may pivot in a second direction opposite the first direction when moving from the collapsed configuration to the expanded configuration.

Alternatively or additionally, the plurality of anchoring frame members may include anchor hooks extending from a distal end of at least some of the plurality of anchoring frame members.

Alternatively or additionally, the expandable frame may be biased into the expanded configuration.

Alternatively or additionally, the expandable frame may be biased into the expanded configuration by at least some of the frame members having a remembered shape.

Alternatively or additionally, the expandable frame may further include a biasing member that is adapted to bias the expandable frame into the expanded configuration.

Alternatively or additionally, the biasing member may be a spring.

Alternatively or additionally, the biasing member may include a threaded screw and tether arrangement.

Alternatively or additionally, the implantable medical device may be an LAAC (left atrial appendage closure) device.

Another example may be found in a left atrial appendage closure (LAAC) device. The LAAC device includes an expandable frame moveable between a collapsed configuration for delivery and an expanded configuration for deployment. The expandable frame includes a plurality of frame members each having a proximal end and a distal end, and a securement member that is adapted to secure the plurality of frame members and to allow the expandable frame to move between the collapsed configuration and the expanded configuration. The LAAC includes a biasing member that is adapted to move the expandable frame into the expanded configuration when not otherwise constrained, and a covering that extends over the proximal end of at least some of the plurality of frame members.

Alternatively or additionally, the biasing member may include a spring.

Alternatively or additionally, the biasing member may include a threaded screw and tether arrangement.

Alternatively or additionally, at least some of the plurality of frame members may be adapted to pivot relative to the securement member in response to a biasing force applied by the biasing member.

Alternatively or additionally, the plurality of frame members may include a plurality of sealing frame members over which the covering extends and a plurality of anchoring frame members that are adapted to anchor the implantable medical device in place.

Alternatively or additionally, the plurality of sealing frame members may be adapted to pivot in a first direction and the plurality of anchoring frame members are adapted to pivot in a second direction opposite the first direction when moving from the collapsed configuration to the expanded configuration.

Another example may be found in a left atrial appendage closure (LAAC) device. The LAAC device includes an expandable frame moveable between a collapsed configuration for delivery and an expanded configuration for deployment, the expandable frame including a plurality of frame members each having a proximal end and a distal end, each of the plurality of frame members adapted to be biased to the expanded configuration when not otherwise constrained. A covering extends over the proximal end of at least some of the plurality of frame members.

Alternatively or additionally, the expandable frame may include a shape memory material.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
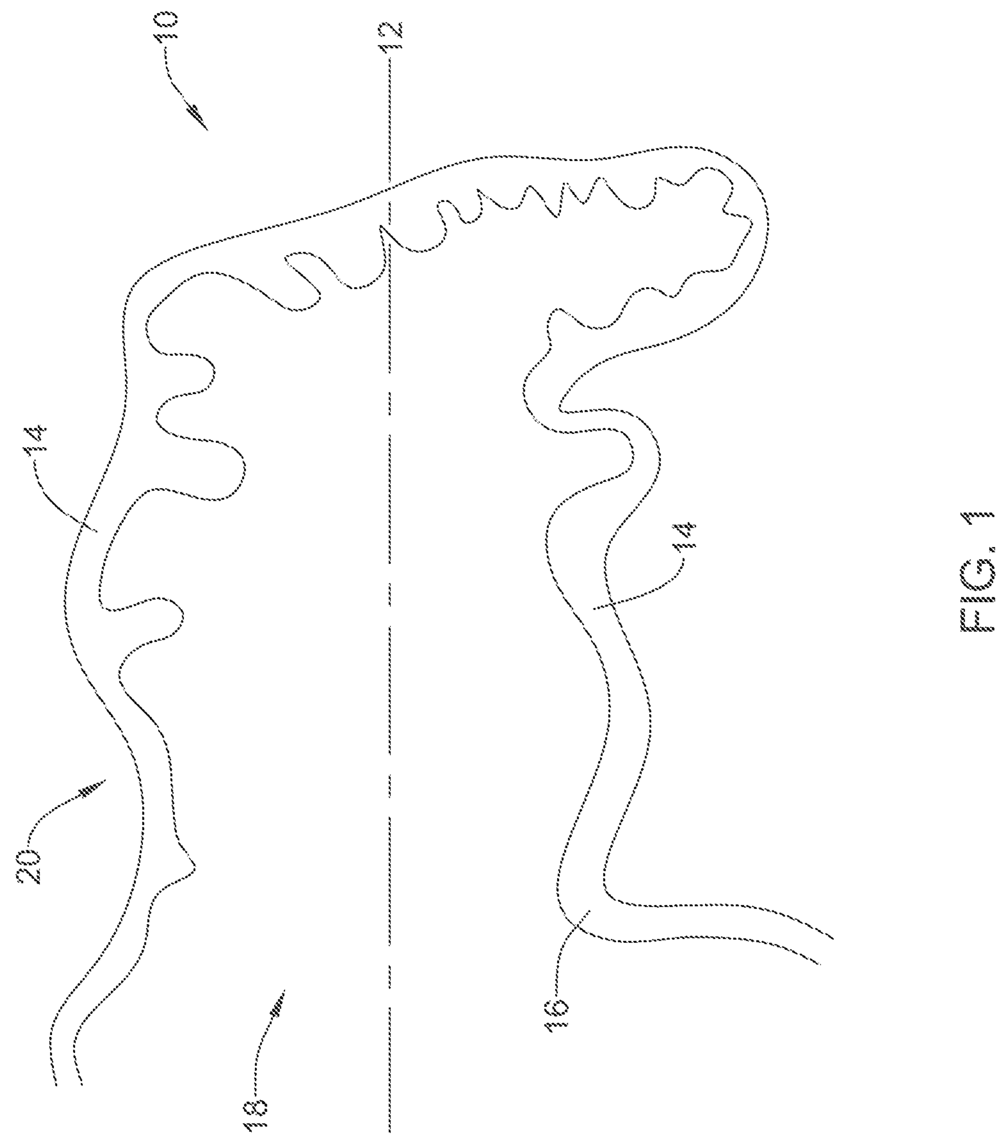
FIG. 1 is a partial cross-sectional view of an LAA (left atrial appendage)

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

The following description should be read with reference to the drawings, which are not necessarily to scale, wherein like reference numerals indicate like elements throughout the several views. The detailed description and drawings are intended to illustrate but not limit the present disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the present disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/ manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following figures illustrate selected components and/or arrangements of an implant for occluding the left atrial appendage, a system for occluding the left atrial appendage, and/or methods of using the implant and/or the system. It should be noted that in any given figure, some features may not be shown, or may be shown schematically, for simplicity. Additional details regarding some of the components of the implant and/or the system may be illustrated in other figures in greater detail. While discussed in the context of occluding the left atrial appendage, the implant and/or the system may also be used for other interventions and/or percutaneous medical procedures within a patient. Similarly, the devices and methods described herein with respect to percutaneous deployment may be used in other types of surgical procedures, as appropriate. For example, in some examples, the devices may be used in a non-percutaneous procedure. Devices and methods in accordance with the disclosure may also be adapted and configured for other uses within the anatomy.

FIG. 1 is a partial cross-sectional view of a left atrial appendage 10. In some embodiments, the left atrial appendage (LAA) 10 may have a complex geometry and/or irregular surface area. It will be appreciated that the illustrated LAA 10 is merely one of many possible shapes and sizes for the LAA 10, which may vary from patient to patient. Those of skill in the art will also recognize that the medical devices, systems, and/or methods disclosed herein may be adapted for various sizes and shapes of the LAA 10, as necessary. The left atrial appendage 10 may include a generally longitudinal axis 12 arranged along a depth of a main body 20 of the left atrial appendage 10. The main body 20 may include a lateral wall 14 and an ostium 16 forming a proximal mouth 18. In some examples, a lateral extent of the ostium 16 and/or the lateral wall 14 may be smaller or less than a depth of the main body 20 along the longitudinal axis 12, or a depth of the main body 20 may be greater than a lateral extent of the ostium 16 and/or the lateral wall 14. In some examples, the LAA 10 may narrow quickly along the depth of the main body 20 or the left atrial appendage may maintain a generally constant lateral extent along a majority of depth of the main body 20. In some examples, the LAA 10 may include a distalmost region formed or arranged as a tail-like element associated with a distal portion of the main body 20. In some examples, the distalmost region may protrude radially or laterally away from the longitudinal axis 12.

Figures 2A, 2B:
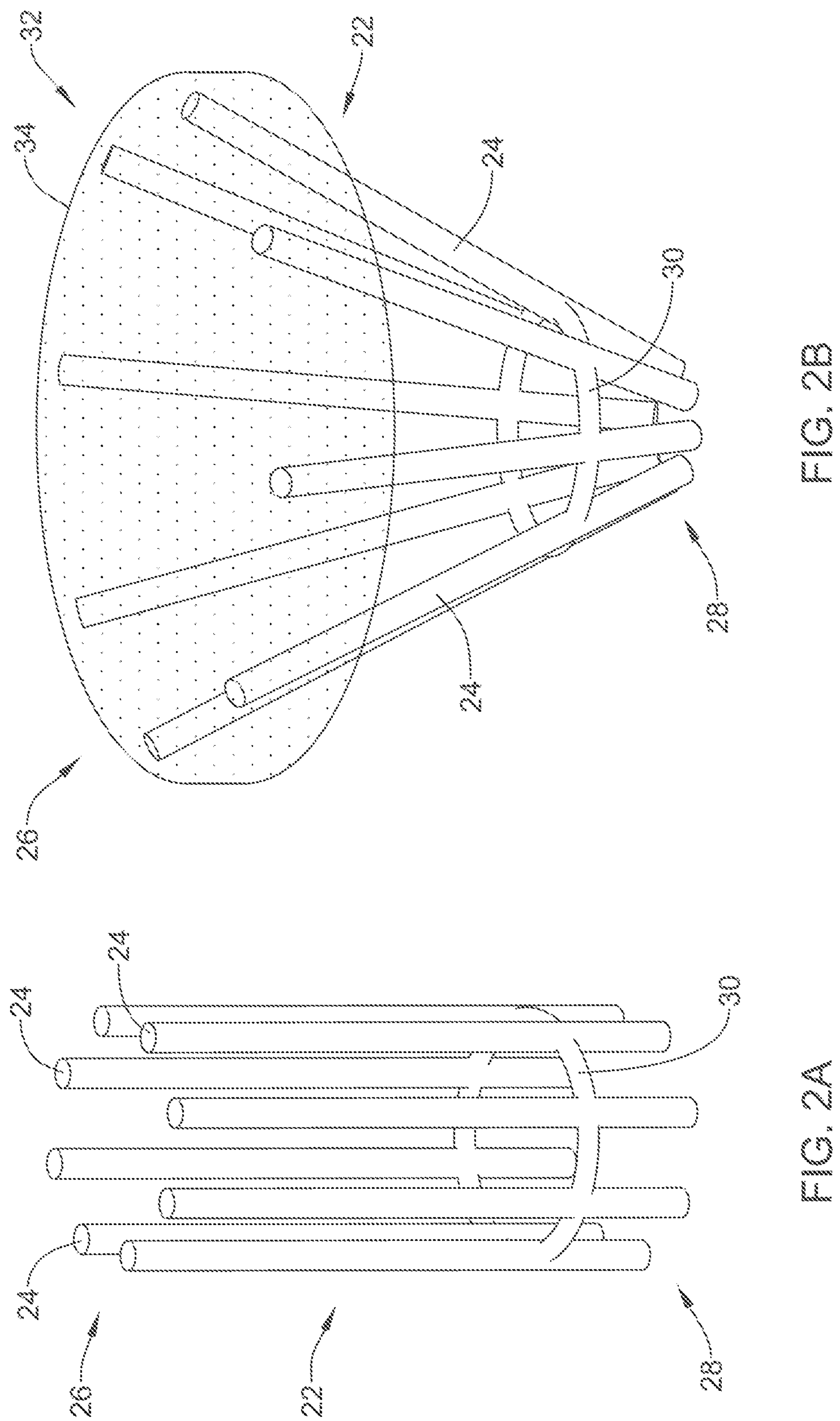
FIGS. 2A and 2B are perspective views of an illustrative expandable frame usable in an LAAC (left atrial appendage closure) device.

FIG. 2A is a perspective view of an illustrative expandable frame 22 that may be used in forming an implantable medical device such as an LAAC (left atrial appendage closure) device that may be implanted near the ostium 16 of the LAA 10 (FIG. 1). The expandable frame 22 includes a plurality of frame members 24, each of which may be considered as extending from a proximal end 26 to a distal end 28. In some instances, as shown, the expandable frame 22 may include a securement member 30 that holds each individual frame member 24 in position relative to the neighboring frame members 24. In some cases, the securement member 30 may be secured to each of the frame members 24. In some cases, the securement member 30 may be adapted to allow each of the frame members 24 to pass through apertures (not shown) that are formed within the securement member 30. In some cases, the securement member 30 may include an inner annular member and an outer annular member, with each of the frame members 24 sandwiched between the inner annular member and the outer annular member. In some instances, the frame members 24 may be adapted to bend or pivot relative to the securement member 30 when the expandable frame 22 moves from its collapsed or delivery configuration, as shown in FIG. 2A, to its expanded or deployment configuration, as shown in FIG. 2B.

FIG. 2B is a perspective view of an illustrative LAAC device 32 that includes the expandable frame 22. The LAAC device 32 includes a covering 34 that spans the proximal ends 26 of the individual frame members 24. The covering 34 may be formed of any suitable material, having any suitable pore size, for example. The covering 34 may be adapted to limit or even prevent blood flow through the covering 34. The covering 34 may be adapted to prevent any blood clots that form within the LAA 10 from passing through the covering 34, and thus prevent any blood clots that form within the LAA 10 from escaping the LAA 10 and entering the blood stream.

In FIG. 2B, the expandable frame 22 can be seen as being in its expanded configuration. In comparing FIG. 2B with FIG. 2A, it can be seen that the frame members 24 have pivoted relative to the securement member 30, with the proximal ends 26 of each of the frame members 24 moving radially outwardly and the distal ends 28 of each of the frame members 24 moving radially inwardly. In some cases, each of the frame members 24 may pivot in unison, and may move the same direction. In some cases, at least some of the frame members 24 may pivot differing amounts, in response to a biasing force, as at least some of the frame members 24 may engage tissue near the ostium 16 of the LAA 10. The LAAC device 32 may include a biasing member (not shown in FIG. 2A or 2B) that provides a biasing force to bias the LAAC 32 into its expanded configuration when not otherwise constrained, such as by a sheath or delivery device.

Figure 2D:
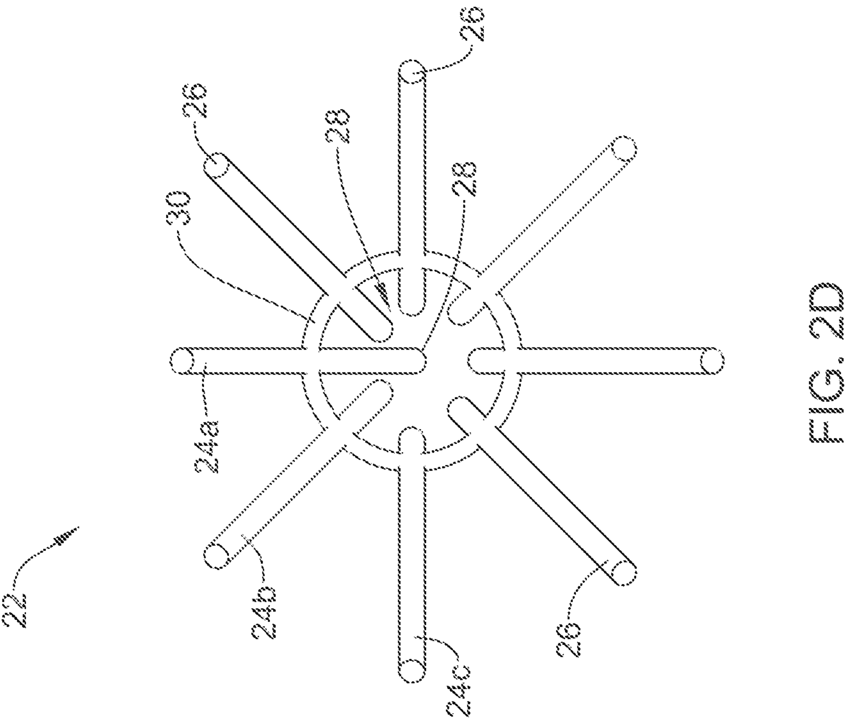
FIGS. 2C and 2D are end views of the illustrative expandable frame shown in FIGS. 2A and 2B.
Figure 2C:
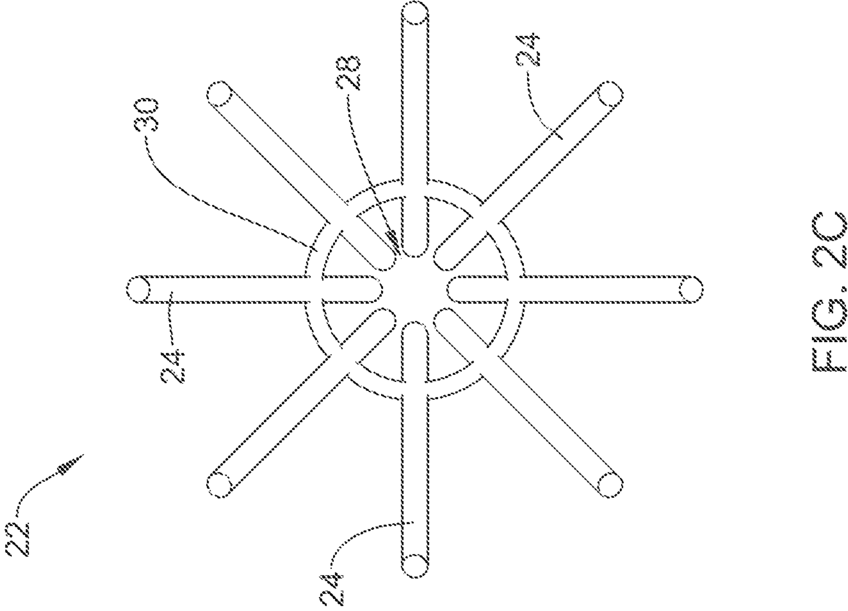

FIGS. 2C and 2D are end views of the expandable frame 22, looking at the expandable frame from a position proximal to the expandable frame 22. In FIG. 2C, each of the frame members 24 may be seen as having moved an equal distance. This can be seen by comparing the relative positions of each of the distal ends 28 of each of the frame members 24, as the distal ends 28 of each of the frame members 24 can be seen as being equidistant from the securement member 30, and from each other. In contrast, FIG. 2D shows that some of the frame members 24 have not moved the same distance. As each of the frame members 24 pivot, how far the proximal ends 26 have moved will be seen in the corresponding movement of the distal ends 28. In FIG. 2D, for example, it can be seen that a frame member 24*a* has moved more than the other frame members 24, as the distal end 28 has moved far enough to span about half way across the circle defined by the securement member 30. A frame member 24*b* has moved farther than some of the other frame members 24, but not as far as the frame member 24*a*. A frame member 24*c* has moved less than the frame member 24*b*. As can be seen, each of the frame members 24 can move a different radial distance, depending on the particular anatomy of the ostium 16 of the LAA 10 for a particular patient.

Figure 3B:
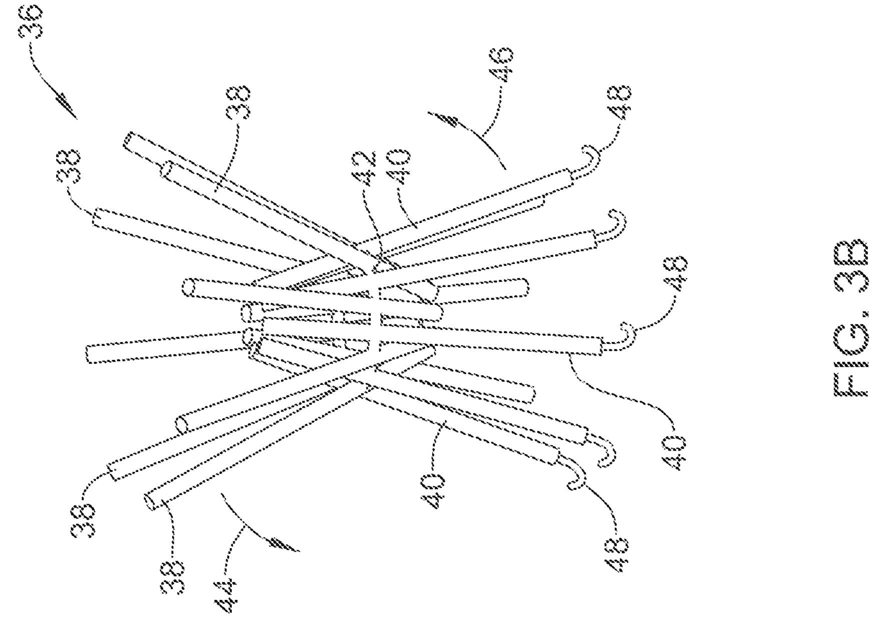
FIGS. 3A and 3B are perspective views of an illustrative expandable frame usable in an LAAC device.
Figure 3A:
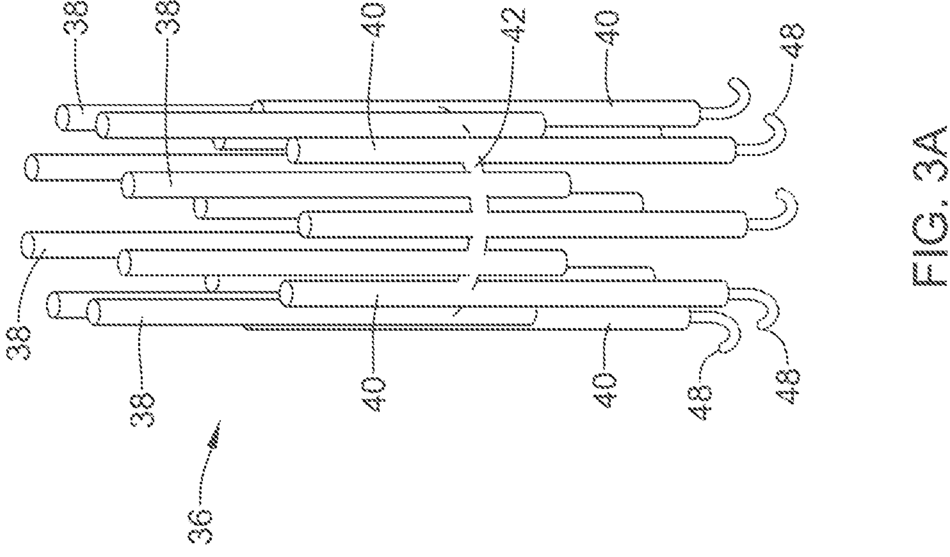

FIG. 3A is a perspective view of an expandable framework 36 that may be combined with a covering (not shown) in order to form an LAAC device. FIG. 3A shows the expandable framework 36 in a collapsed configuration while FIG. 3B shows the expandable framework 36 in an expanded configuration. The expandable framework 36 includes a plurality of sealing frame members 38 and a plurality of anchor frame members 40. The plurality of sealing frame members 38 and the plurality of anchor frame members 40 are each adapted to pivot relative to a securement member 42. The plurality of sealing frame members 38 may be secured to the securement member 42 in a manner that allows the plurality of sealing frame members 38 to pivot in a first direction, indicated by a curved arrow 44, relative to the securement member 42. The plurality of anchor frame members 40 may be secured to the securement member 42 in a manner that allows the plurality of anchor frame members 40 to pivot in a second direction, indicated by a curved arrow 46, relative to the securement member 42.

It will be appreciated that an LAAC device may be formed from the expandable framework 36 by spanning the plurality of sealing frame members 38 with a covering such as the covering 34 shown in FIG. 2B. As the expandable frame 36 is moved into its expanded configuration, such as by application of a biasing force, the free ends of each of the plurality of sealing members 38 will move into contact with the ostium 16 of the LAA 10 as the plurality of sealing members 38 pivot in the direction indicated by the curved arrow 44. Concurrently, the free ends of each of the plurality of anchor frame members 40 will move into contact with the body 20 of the LAA 10, thereby helping to secure the expandable frame 36 in position relative to the LAA 10. Some of the plurality of sealing frame members 38 may move different distances, in response to an applied biasing force, depending on the anatomy of the LAA 10. Some of the plurality of anchor frame members 40 may move in different distances, in response to an applied biasing force, depending on the anatomy of the LAA 10.

In some cases, as shown, the free ends of each of the plurality of anchor frame members 40 may include curved hooks 48 to help in anchoring the expandable frame 36. The curved hooks 48 may be formed by simply curving the free ends of each of the plurality of anchor frame members 40. In some cases, the curved hooks 48 may be separately formed, and may then be welded or otherwise attached to the free ends of each of the plurality of anchor frame members 40. In some cases, each of the anchor frame members 40 may include one of the curved hooks 48. In some instances, only some of the anchor frame members 40 may include one of the curved hooks 48. The curved hooks 48 may take any shape, and are not limited to that shown in FIGS. 3A and 3B.

Figure 4:
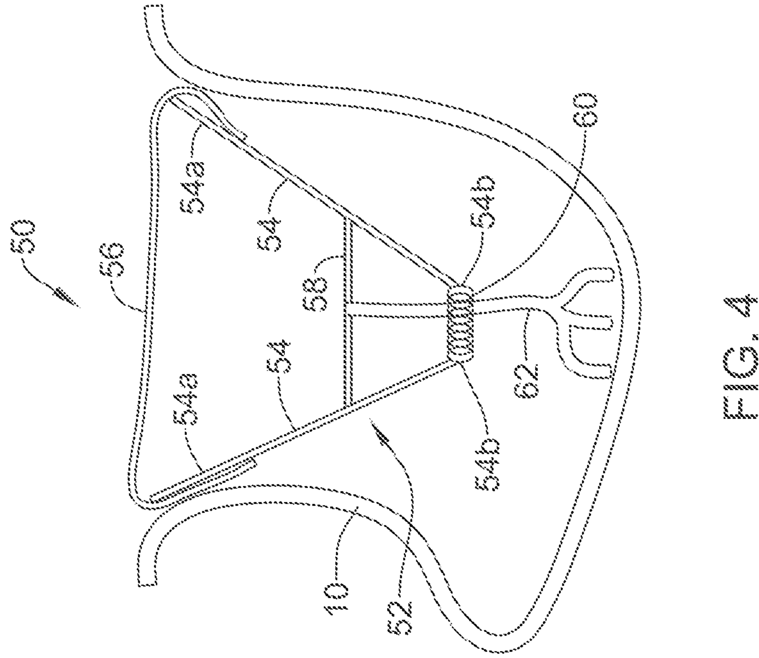
FIG. 4 is a schematic view of an illustrative LAAC device shown within an LAA.

FIG. 4 is a schematic view of an illustrative LAAC device 50 disposed within the LAA 10. The illustrative LAAC device 50 shows an example of a biasing mechanism that may be used in combination with the expandable framework 22, for example. The LAAC device 50 includes an expandable framework 52 that includes several frame members 54. It will be appreciated that the expandable framework 52 will likely include additional frame members 54 beyond the two that are illustrated. The LAAC device 50 includes a covering 56 that spans a proximal end 54*a* of each of the frame members 54 and is adapted to seal across the LAA 10.

The expandable framework 52 includes a pivot base 58 that provides a point against which each of the frame members 54 are free to pivot in response to an applied biasing force. The expandable framework 52 includes a spring 60 that is adapted to provide a biasing force. In some cases, the spring 60 may be secured relative to a distal end 54*b* of each of the frame members 54. The expandable framework 52 may be moved into a collapsed configuration by moving a proximal end 54*a* of each of the frame members 54 radially inward, thereby causing a distal end 54*b* of each of the frame members 54 radially outwardly to a position in which the frame members 54 may be at least substantially parallel with each other. In the collapsed configuration, it will be appreciated that the spring 60 will be stretched beyond an equilibrium position. This means that the spring 60 will want to contract once the expandable frame 52 is no longer constrained against movement, such as by a sheath extending over the expandable frame 52 and/or placement within a delivery device.

In some cases, the LAAC device 50 may include an anchor tether 62 that extends from the pivot base 58. The anchor tether 62 may be adapted to be secured within the LAA 10, for example, in order to help anchor the LAAC device 50. In some instances, the anchor tether 62 may be adapted to limit relative proximal movement of the LAAC device 50 relative to the LAA 10. In some cases, this may help with holding the LAAC device 50 in place, thereby preventing the LAAC device 50 from being implanted in a position in which the LAAC device 50 does not extend far enough into the LAA 10 so that the covering 56 can seal against the LAA 10.

Figure 5:
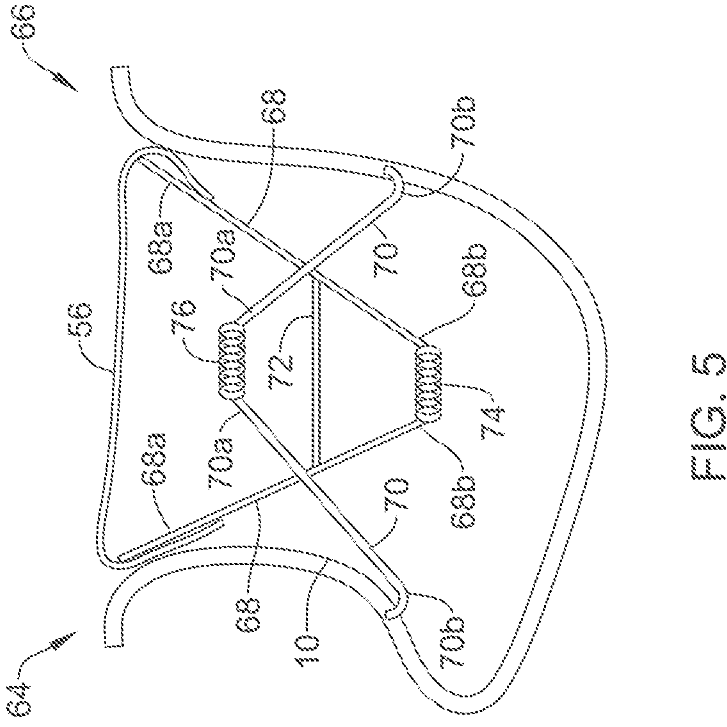
FIG. 5 is a schematic view of an illustrative LAAC device shown within an LAA.

FIG. 5 is a schematic view of an illustrative LAAC device 64 disposed within the LAA 10. The illustrative LAAC device 64 shows an example of a biasing mechanism that may be used in combination with the expandable framework 36, for example. The LAAC device 64 includes an expandable framework 66 that includes several sealing frame members 68 and several anchor frame members 70. It will be appreciated that the expandable framework 66 will likely include additional sealing frame members 68 and additional anchor frame members 70 beyond the two each that are illustrated. The LAAC device 66 includes a covering 56 that spans a proximal end 68*a* of each of the sealing frame members 68 and is adapted to seal across the LAA 10.

The expandable framework 66 includes a pivot base 72 that provides a point against which each of the sealing frame members 68 and each of the anchor frame members 70 are free to pivot in response to an applied biasing force. The expandable framework 66 includes a first spring 74 that is adapted to provide a biasing force. The first spring 74 extends between a distal end 68*b* of each of the sealing frame members 68. The expandable framework 52 may be moved towards a collapsed configuration by moving a proximal end 68*a* of each of the sealing frame members 68 radially inward, thereby causing the distal end 68*b* of each of the sealing frame members 68 to move radially outwardly to a position in which the sealing frame members 68 may be at least substantially parallel with each other. In the collapsed configuration, it will be appreciated that the first spring 74 will be stretched beyond an equilibrium position. This means that the first spring 74 will want to contract once the expandable frame 66 is no longer constrained against movement, such as by a sheath extending over the expandable frame 66 and/or placement within a delivery device.

The expandable framework 66 includes a second spring 76 that is that is adapted to provide a biasing force. The second spring 76 extends between a distal end 70*b* of each of the anchor frame members 70. The expandable framework 66 may be moved towards a collapsed configuration by moving a distal end 70*b* of each of the anchor frame members 70 radially outwardly, thereby causing a proximal end 70*b* of each of the anchor frame members 70 to move radially inwardly to a position in which the anchor frame members 70 may be at least substantially parallel with each other. In the collapsed configuration, it will be appreciated that the first spring 74 will be stretched beyond an equilibrium position. This means that the second spring 76 will want to contract once the expandable frame 66 is no longer constrained against movement, such as by a sheath extending over the expandable frame 66 and/or placement within a delivery device.

Figures 6A, 6B:
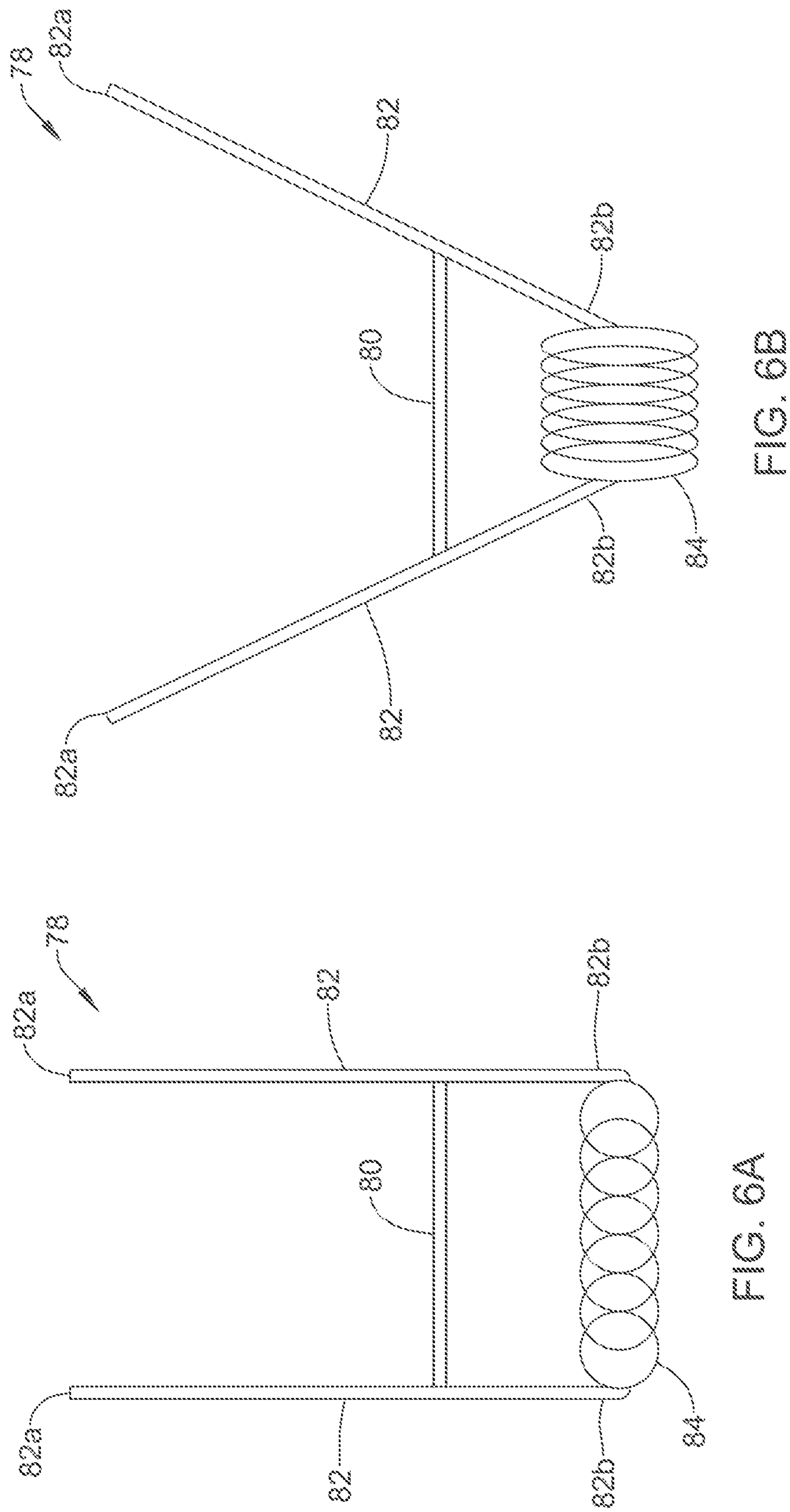
FIGS. 6A and 6B are schematic views of an illustrative expandable frame usable in an LAAC device.

FIGS. 6A and 6B show an example of an expandable framework 78 that includes a pivot base 80 against which several frame members 82 are free to pivot. The expandable framework 78 is shown in FIG. 6A in a collapsed configuration and in FIG. 6B in an expanded configuration. A biasing member 84 is shown extending between a distal end 82*b* of each of the frame members 82. In some cases, while only two frame members 82 and one biasing member 84 is shown, it will be appreciated that in some cases, there may be multiple pairs of frame members 82, with a biasing member 84 extending between a first frame member 82 and a second frame member 82 of a pair of frame members 72. For example, a first biasing member 84 may extend between the two frame members 82 of a first pair, and a second biasing member 84 may extend between the two frame members 82 of a second pair, and so on.

Figures 7A, 7B:
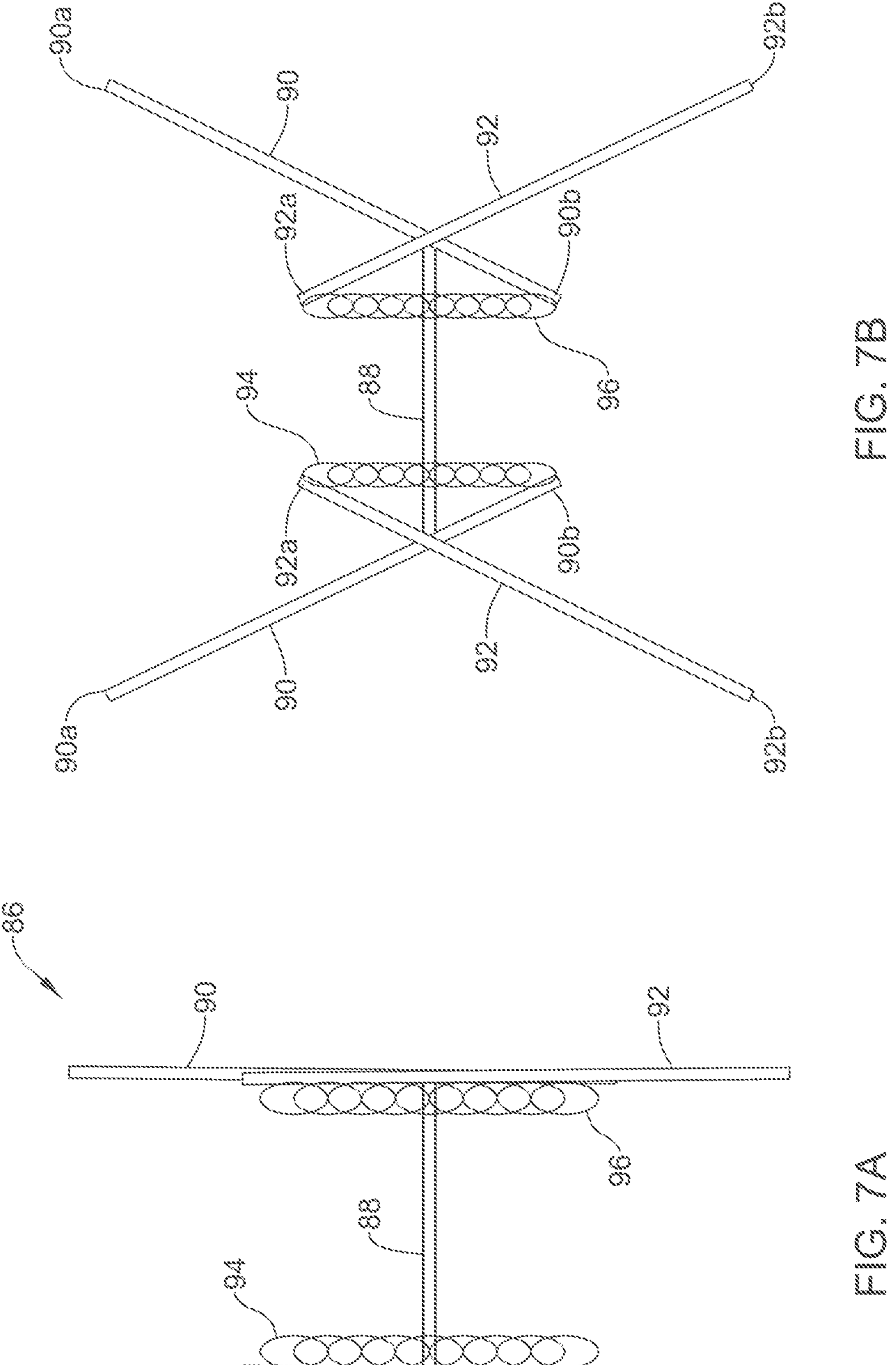
FIGS. 7A and 7B are schematic views of an illustrative expandable frame usable in an LAAC device.

FIGS. 7A and 7B show an example of an expandable framework 86 that includes a pivot base 88 against which several sealing frame members 90 and several anchor frame members 92 are free to pivot. The expandable framework 86 is shown in FIG. 7A in a collapsed configuration and in FIG. 7B in an expanded configuration. A first biasing member 94 extends between a proximal end 92*a* of an anchor frame member 92 and a distal end 90*b* of a sealing frame member 90*b*. A second biasing member 96 extends between a proximal end 92*a* of another anchor frame member 92 and a distal end 90*b* of another sealing frame member 90.

It will be appreciated that in the collapsed configuration shown in FIG. 7A, in which the sealing frame members 90 and the anchor frame members 92 are at least substantially parallel with each other, that the first biasing member 94 and the second biasing member 96 are stretched beyond their equilibrium length. As a result, as soon as the expandable framework 86 is no longer constrained against movement by a sheath disposed thereover, or the expandable framework 96 being disposed within a delivery device, the first biasing member 94 and the second biasing member 96 will each exert a biasing force. This causes the distal end 90*b* of each of the sealing frame members 90 to move radially inwardly (causing the proximal ends 90*a* to move radially outwardly) and causes the proximal end 92*a* of each of the anchor frame members 92 to move radially inwardly (causing the distal ends 92*b* to move radially outwardly).

Figures 8A, 8B:
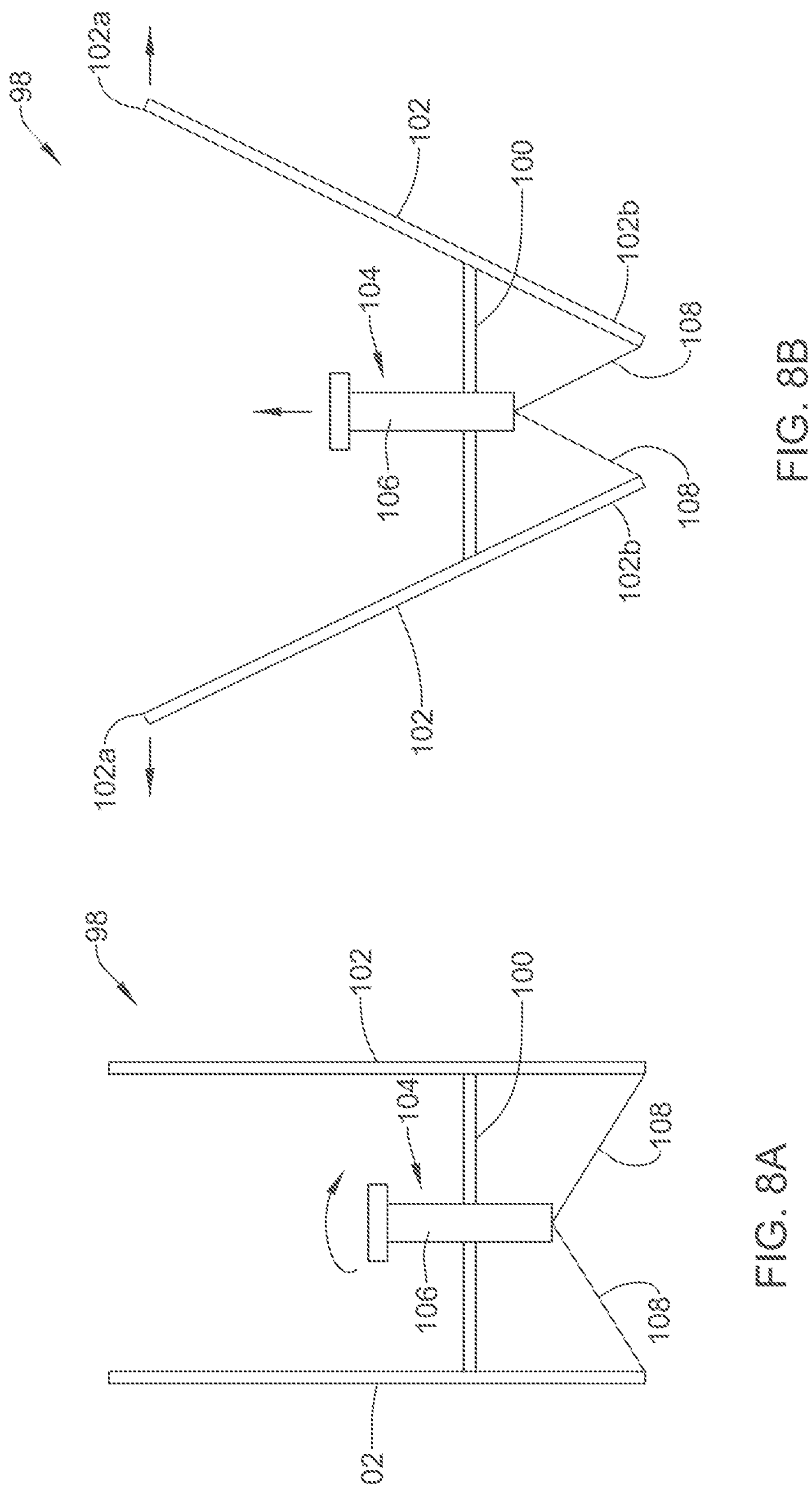
FIGS. 8A and 8B are schematic views of an illustrative expandable frame usable in an LAAC device.

FIGS. 8A and 8B show an example of an expandable framework 98 that includes a pivot base 100 against which several frame members 102 are free to pivot. The expandable framework 98 is shown in FIG. 8A in a collapsed configuration and in FIG. 8B in an expanded configuration. The expandable framework 98 includes a biasing member 104 that may be actuated to move the expandable framework 98 from its collapsed configuration to its expanded configuration, or vice versa. The biasing member 104 includes a threaded fastener 106 that is adapted to threadedly engage the pivot base 100. The biasing member 104 also includes one or more tethers 108 that extend from the threaded fastener 106 to a distal end 102*b* of each of the frame members 102.

Rotating the threaded fastener 106 relative to the pivot base 100 causes the vertical (in the illustrated orientation) position of the threaded fastener 106 to change relative to the pivot base 100. By causing the threaded fastener 106 to move vertically upward, as can be seen by comparing FIG. 8A and FIG. 8B), the tethers 108 exert a biasing force on the distal end 102*b* of each of the frame members 102. This causes the distal end 102*b* of each of the frame members 102 to move radially inwardly, which of course causes a proximal end 102*a* of each of the frame members 102 to move radially outwardly into contact with the ostium 16 of the LAA 10. A tool such as a screwdriver or nut driver may be used to rotate the threaded fastener 106. It will be appreciated that the biasing member 104 could be used with the expandable frame 22.

Figure 9B:
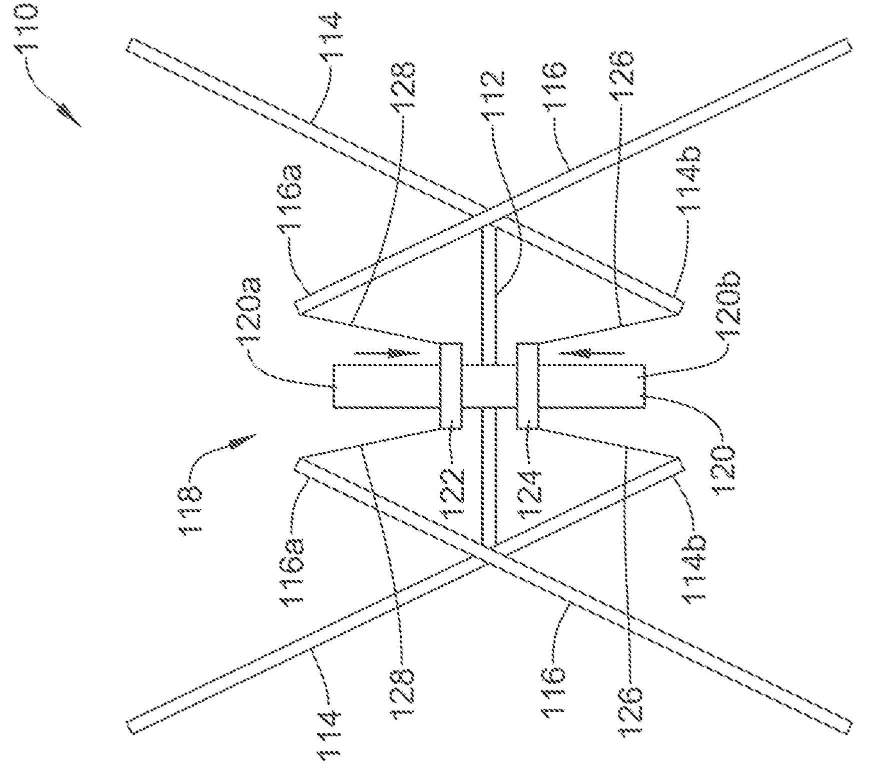
FIGS. 9A and 9B are schematic views of an illustrative expandable frame usable in an LAAC device.
Figure 9A:
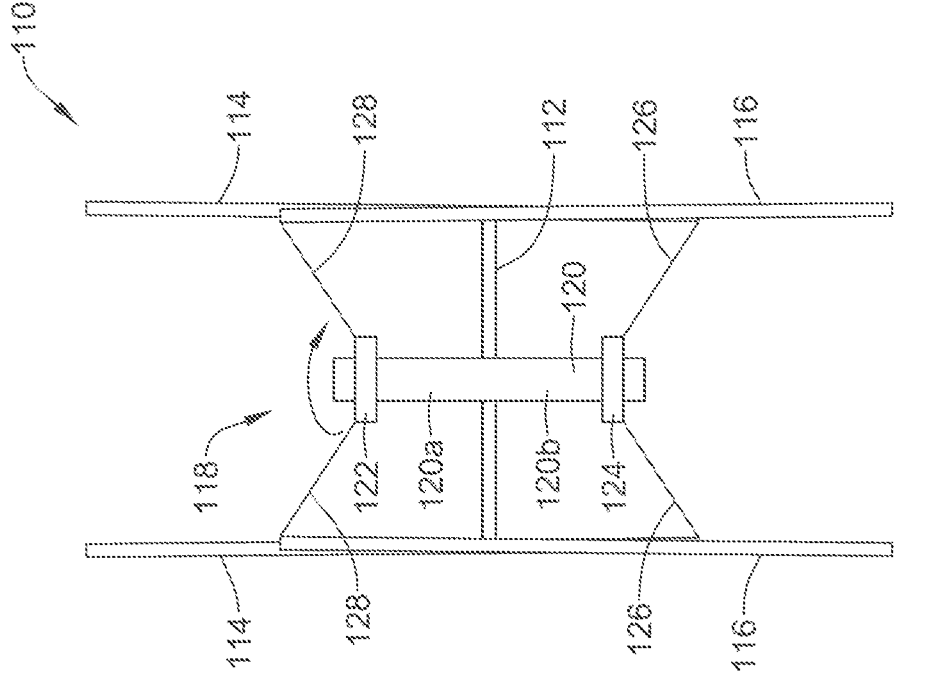

FIGS. 9A and 9B show an example of an expandable framework 110 that includes a pivot base 112 against which several sealing frame members 114 and several anchor frame members 116 are free to pivot. The expandable framework 110 is shown in FIG. 9A in a collapsed configuration and in FIG. 9B in an expanded configuration. The expandable framework 110 includes a biasing member 118 that may be actuated to move the expandable framework 110 from its collapsed configuration to its expanded configuration, or vice versa. The biasing member 118 includes a threaded rod 120 that includes a first portion 120*a* that is located above the pivot base 112 and a second portion 120*b* that is located below the pivot base 112. In some cases, the first portion 120*a* of the threaded rod 120 has a particular-handed thread while the second portion 120*b* of the threaded rod 120 has an opposing-handed thread. One may be right-handed thread while the other is left-handed thread, for example.

The biasing member 118 includes a first threaded nut 122 that threadedly engages the first portion 120*a* of the threaded rod 120 as well as a second threaded nut 124 that threadedly engages the second portion 120*b* of the threaded rod 120. It will be appreciated that the first threaded nut 122 may have a thread-handedness that matches that of the first portion 120*a* of the threaded rod 120 while the second threaded nut 124 may have a thread-handedness that matches that of the second portion 120*b* of the threaded rod 120. The biasing member 118 includes a tether 126 that extends between the second threaded nut 124 and a distal end 114*b* of each of the sealing frame members 114. The biasing member 118 includes a tether 128 that extends between the first threaded nut 122 and the proximal end 116*a* of each of the anchor frame members 114.

By rotating the threaded rod 120, the first threaded nut 122 may be caused to move in a downward direction and the second threaded nut 124 may be caused to move in an upward direction. The downward movement of the first threaded nut 122 causes the proximal ends 116*a* of the anchor frame members 116 to move radially inward, which causes the corresponding distal ends 116*b* of the anchor frame members 116 to move radially outwardly. The upward movement of the second threaded nut 124 causes the distal ends 114*b* of the sealing frame members 114 to move radially inward, which causes the corresponding proximal ends 114*a* of the sealing frame members 114 to move radially outward and into contact with the ostium 16 of the LAA 10. A tool such as a screwdriver or nut driver may be used to rotate the threaded rod 120.

Figures 10A, 10B, 10C:
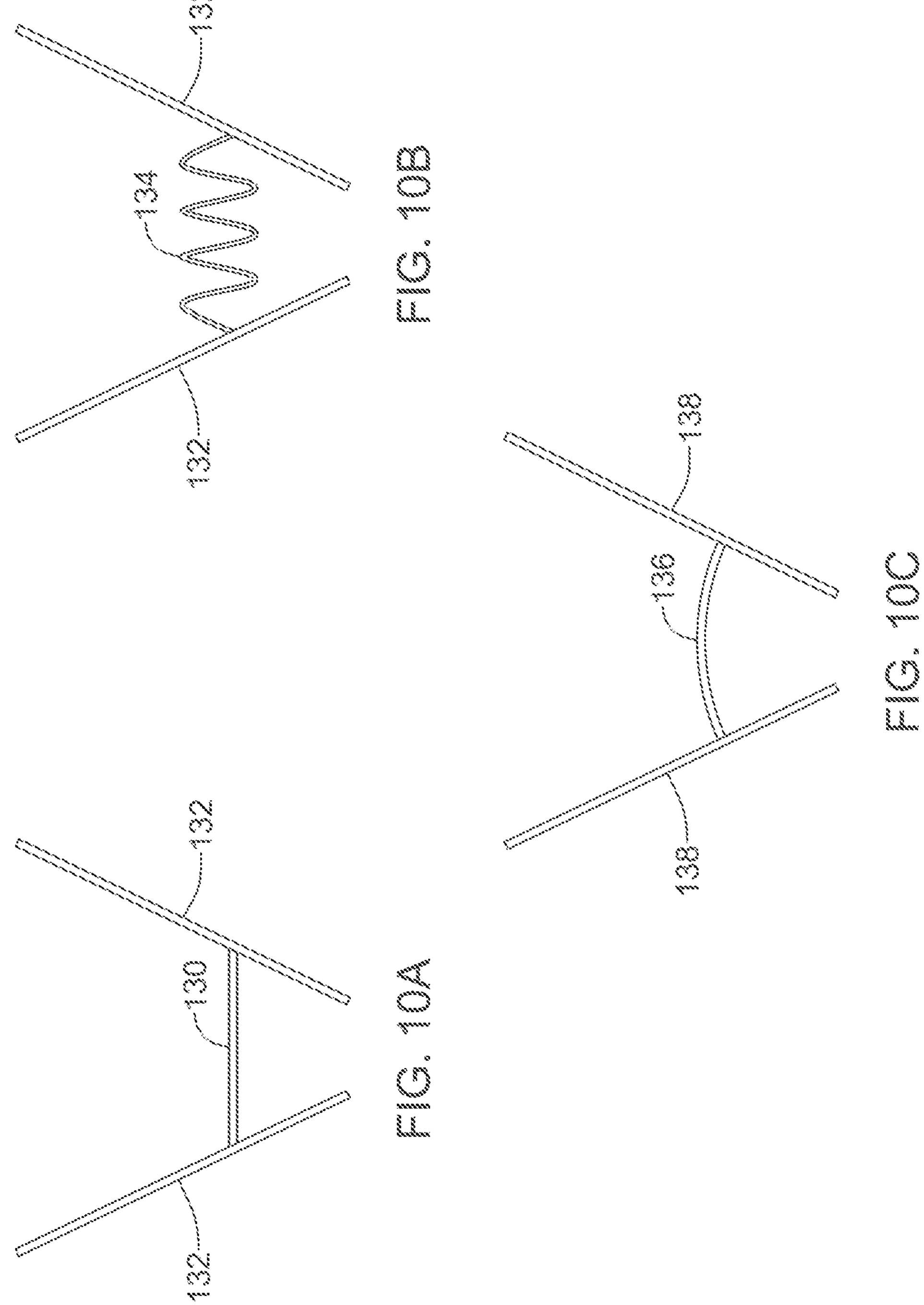
FIGS. 10A, 10B and 10C are schematic views of illustrative expandable frames usable in an LAAC device.

FIGS. 10A, 10B and 10C are schematic views of illustrative pivot base configurations. FIG. 10A shows a rigid or semi-rigid pivot base 130 that provides a pivot point for several frame members 132. FIG. 10B shows a collapsing pivot base 134 that provides a pivot point for the frame members 132. FIG. 10C shows a monolithic base 136 that is formed as a single piece with the frame members 138. The monolithic base 136 may be considered as flexing with the frame members 138 as the frame members 138 move.

Figure 11B:
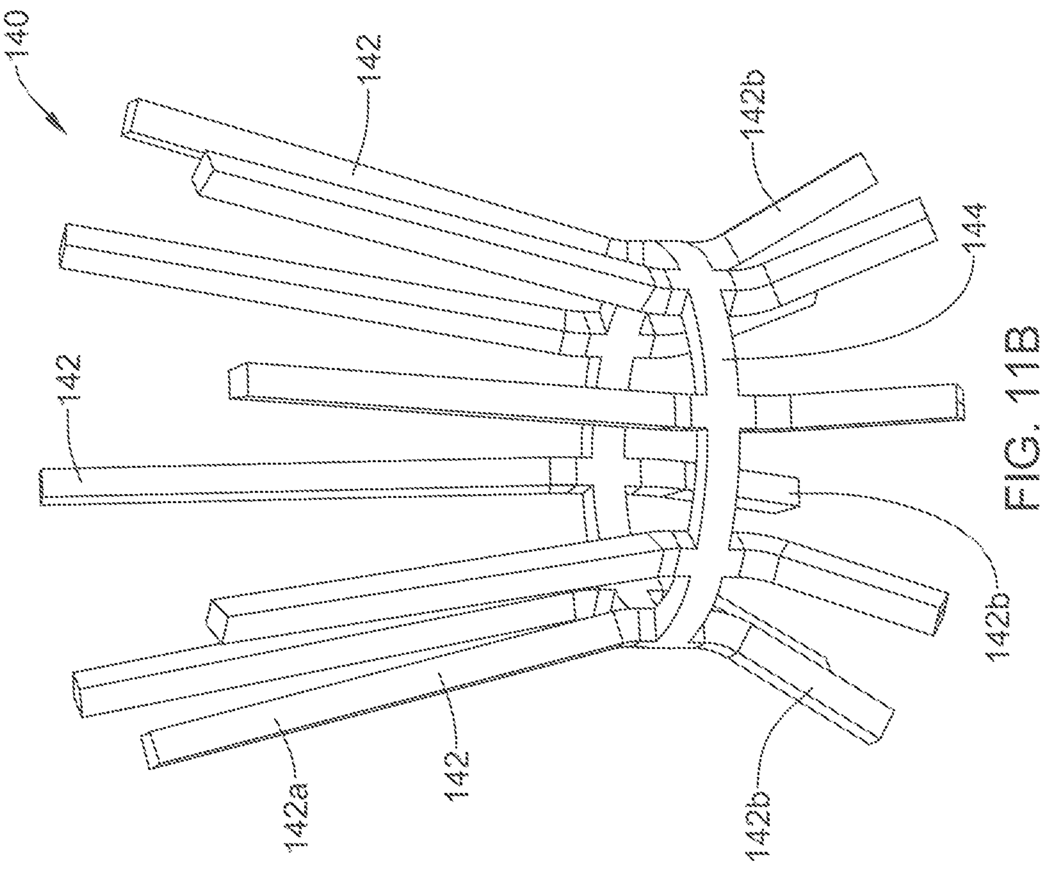
FIGS. 11A, 11B and 11C are schematic views of an illustrative expandable frame usable in an LAAC device.
Figure 11A:
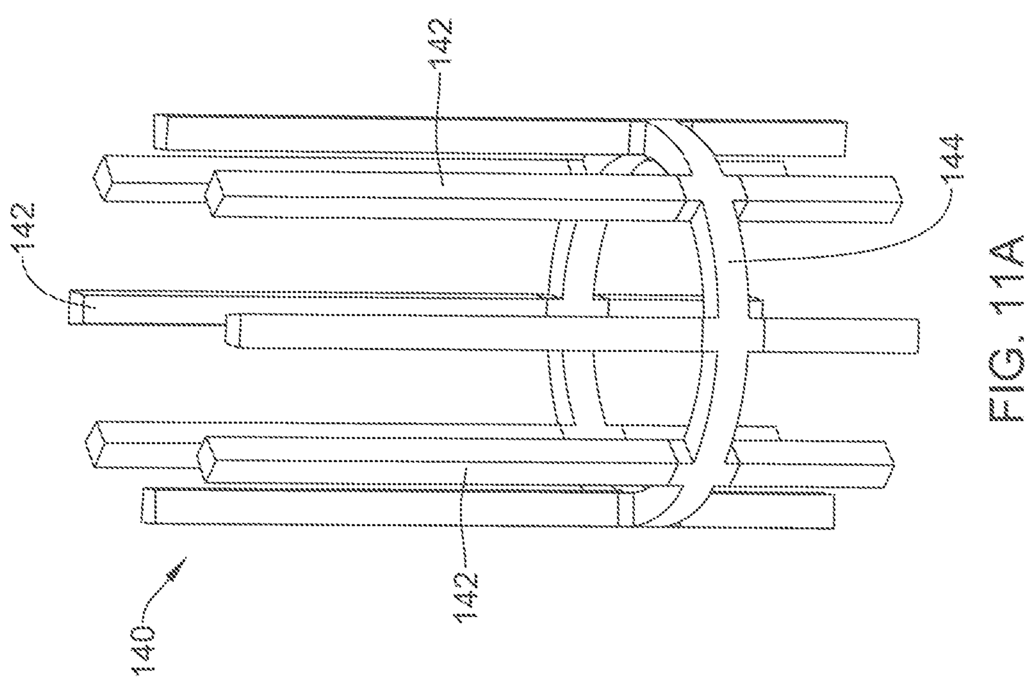
Figure 11C:
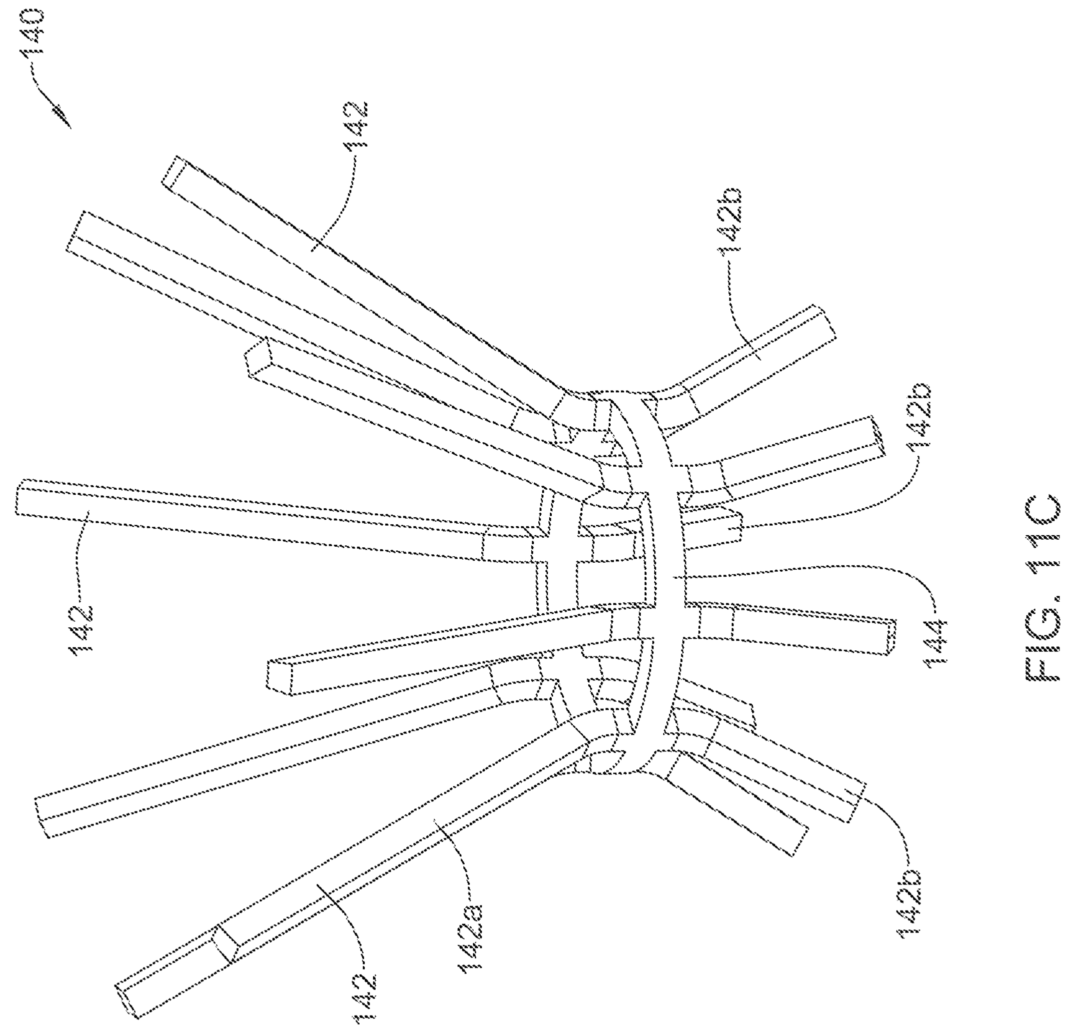

FIGS. 11A, 11B and 11C are perspective views of an illustrative monolithic expandable frame 140. FIG. 11A shows the expandable frame 140 in a collapsed configuration. FIG. 11B shows the expandable frame 140 in a first expanded configuration and FIG. 11C shows the expandable frame 140 in a second expanded configuration that is more fully expanded than the first expanded configuration. FIG. 11B may be considered as showing an expanded configuration with the expanded frame 140 disposed within a LAA 10 of a first patient, and FIG. 11C may be considered as showing an expanded configuration with the expanded frame 140 disposed within a relatively larger LAA 10 of a second patient, for example.

The expandable frame 140 includes a number of frame members 142 and a securement member 144 that joins the frame members 142 together. In some cases, the expandable frame 140 may be formed of nitinol or stainless steel, for example, and may be laser cut from a single piece of material. The flat piece of material, after laser cutting, may be rolled into a cylindrical shape (such as that shown in FIG. 11A) and welded together to form the expandable frame 140. In some cases, the expandable frame 140 may have a remembered shape that corresponds to the expanded configuration, and may be biased into regaining its remembered shape as soon as the expandable frame 140 is not otherwise constrained by a sheath extending thereover, or being loaded into a delivery device.

In some cases, each of the frame members 142 may be considered as including a sealing portion 142*a* that extends above (in the illustrated orientation) the securement member 144 and an anchor portion 142*b* that extends below the securement member 144. As the expandable frame 140 is unconstrained, the sealing portions 142*a* will move radially outwardly until each sealing portion 142*a* contacts tissue, and the anchor portions 142*b* will also move radially outwardly until each anchor portion 142*b* also contacts tissue. This allows any membrane or covering (not shown) extending over the sealing portions 142*a* to seal against the ostium 16 of the LAA 10. This also allows the anchor portions 142*b* to help anchor the expandable frame 140 in position within the LAA 10.

Figures 12A, 12B:
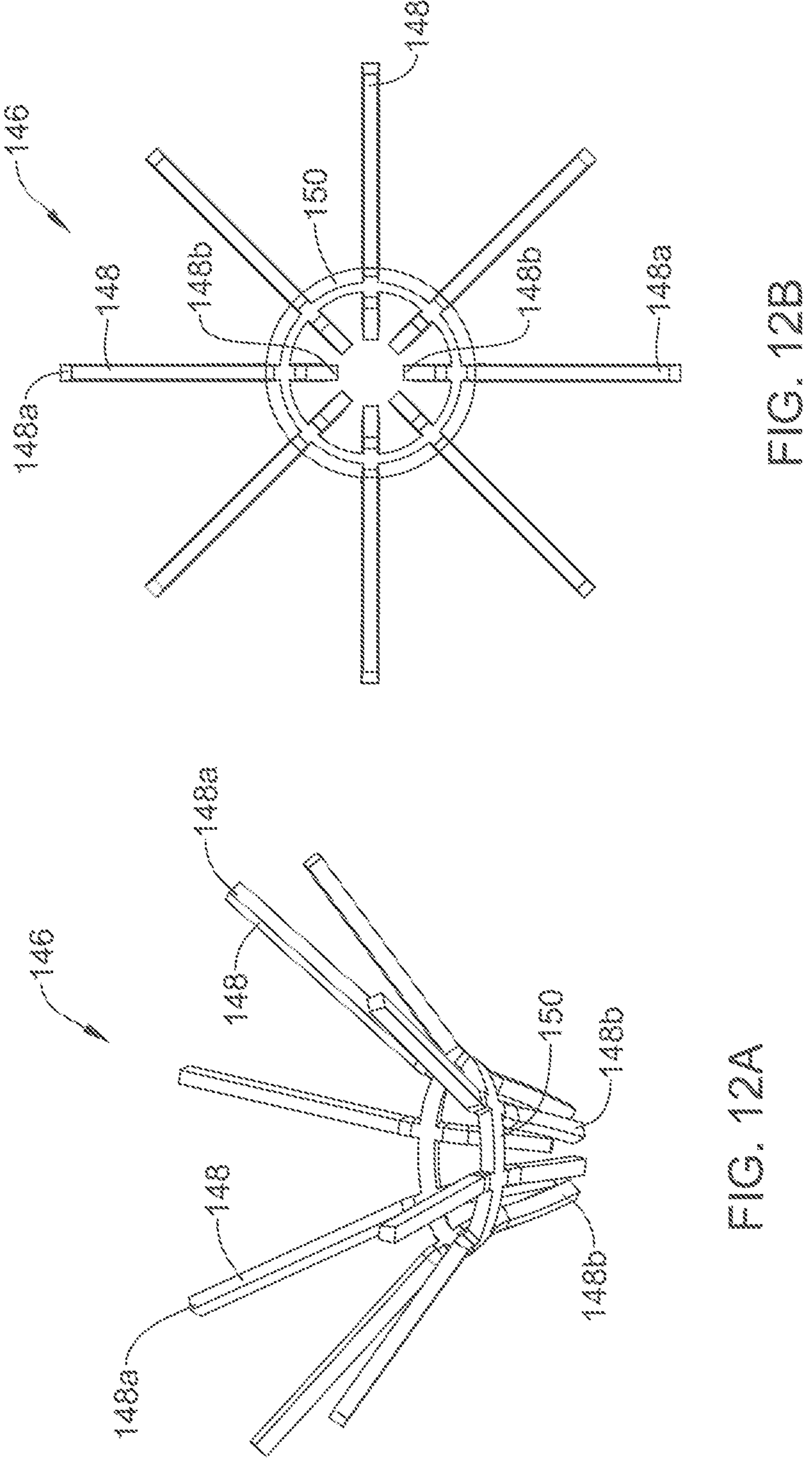
FIG. 12A is a perspective view of an illustrative expandable frame usable in an LAAC device.
FIG. 12B is an end view of the illustrative expandable frame shown in FIG. 12A.

FIG. 12A is a perspective view of an illustrative monolithic expandable frame 146 shown in an expanded configuration and FIG. 12B is an end view of the expandable frame 146 in the expanded configuration, showing a view from a position distal of the expandable frame 146. The expandable frame 146 includes a number of frame members 148 that extend from a securement member 150. FIGS. 12A and 12B show a relatively even expansion into the expanded configuration in which each of the distal ends 148*b* of the frame members 148 extend essentially the same distance into a circle defined by the securement member 150. As a result, the proximal ends 148*a* each extend radially outwardly from the securement member 150 a similar distance. This may be considered as being a round expansion.

Figure 13B:
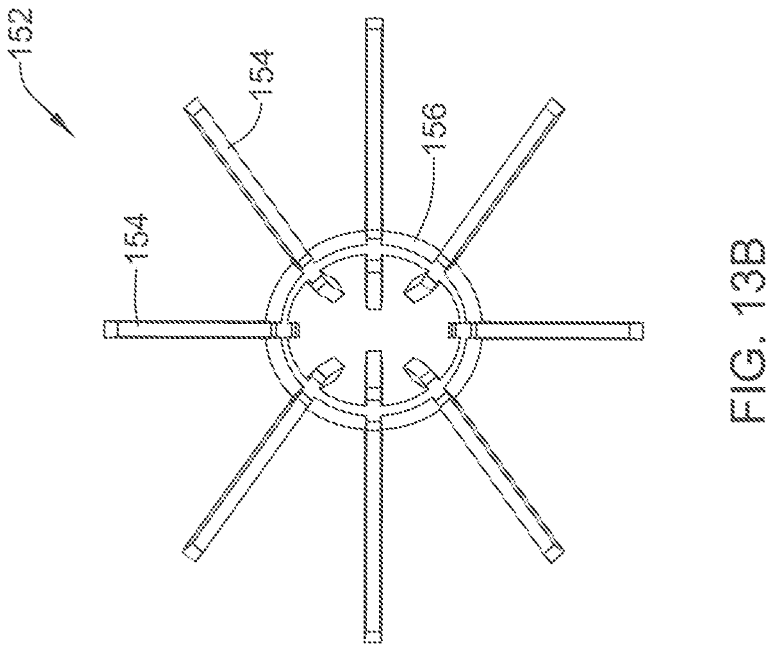
FIG. 13B is an end view of the illustrative expandable frame shown in FIG. 13A.
Figure 13A:
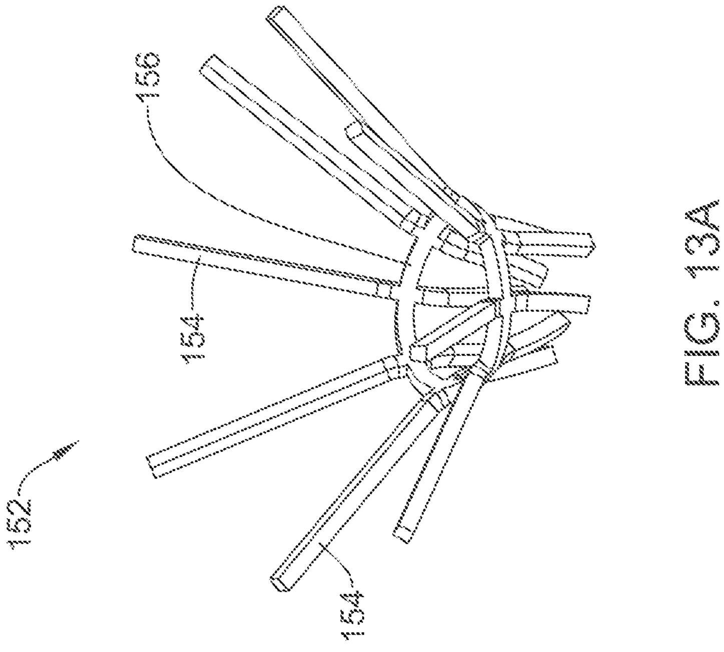
FIG. 13A is a perspective view of an illustrative expandable frame usable in an LAAC device.

FIG. 13A is a perspective view of an illustrative monolithic expandable frame 152 shown in an expanded configuration and FIG. 13B is an end view of the expandable frame 152 in the expanded configuration, showing a view from a position distal of the expandable frame 152. The expandable frame 152 includes a number of frame members 154 that extend from a securement member 156. FIGS. 13A and 13B show a relatively uneven expansion into the expanded configuration in differences in movement of the individual frame members 154 has distorted the securement member 156 out of a circular profile. Rather, the securement member 156 may be seen as being distorted as a result of various frame members 154 moving different distances as a result of the anatomy of the LAA 10. This may be considered as being an elliptical expansion.

Figures 14A, 14B, 14C:
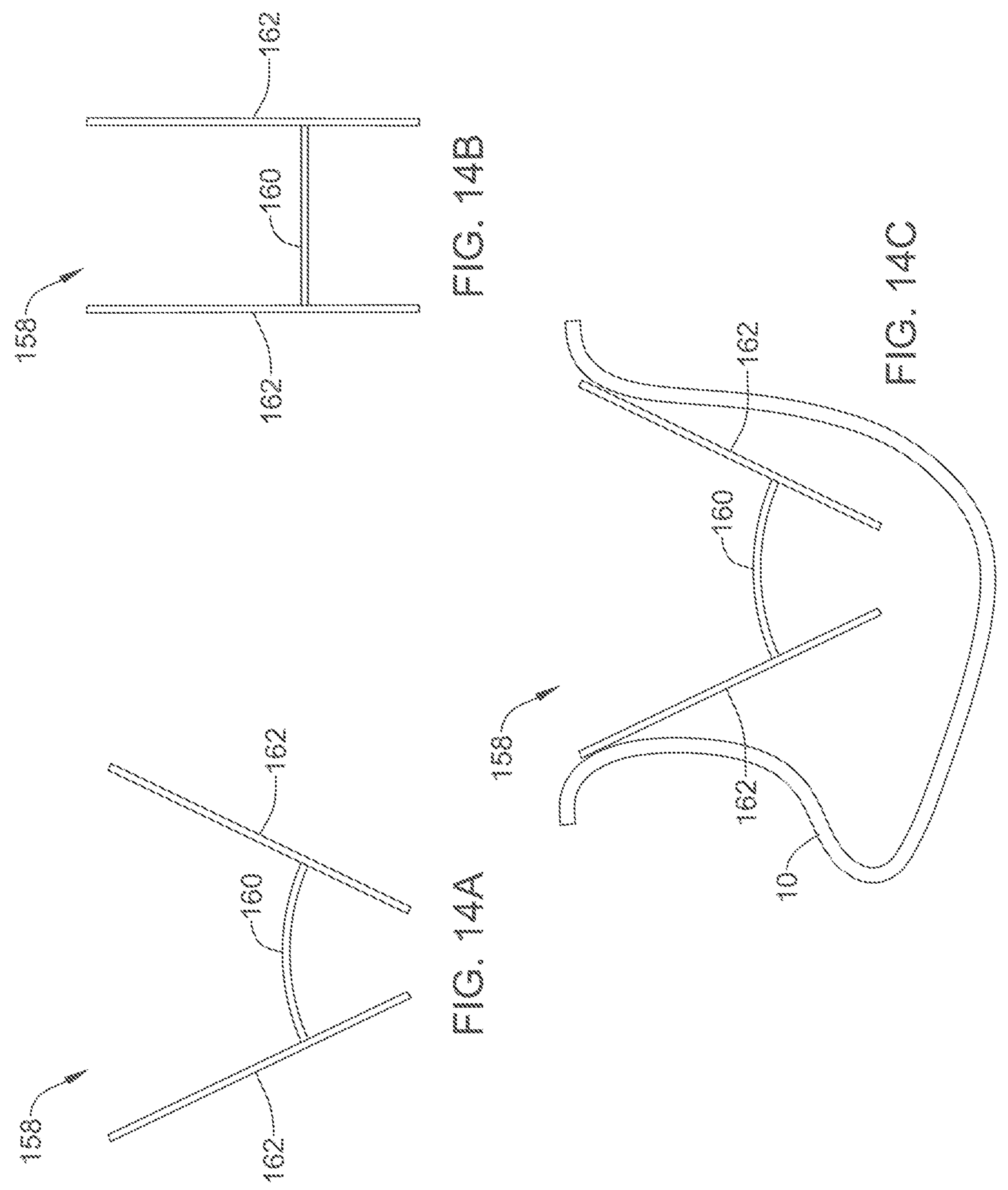
FIGS. 14A, 14B and 14C are schematic views of an illustrative expandable frame usable in an LAAC device.

FIGS. 14A, 14B and 14C are schematic views of an illustrative expandable frame 158 that includes a pivot base 160 and several frame members 162 extending from the pivot base 160. The pivot base 160 may be considered as being an example of the monolithic base 136 (FIG. 10C). In FIG. 14A, the expandable frame 158 is shown in its remembered shape, or expanded configuration, which is the shape that the expandable frame 158 will return to absent any constraining forces. FIG. 14B shows the expandable frame 158 in a collapsed configuration. FIG. 14C shows the expandable frame 158 deployed within the LAA 10. The expandable frame 158 has partially regained its expanded configuration, due to some constraints provided on the expandable frame 158 by virtue of the frame members 162 having contacted anatomy within the LAA 10.

Figures 15A, 15B, 15C:
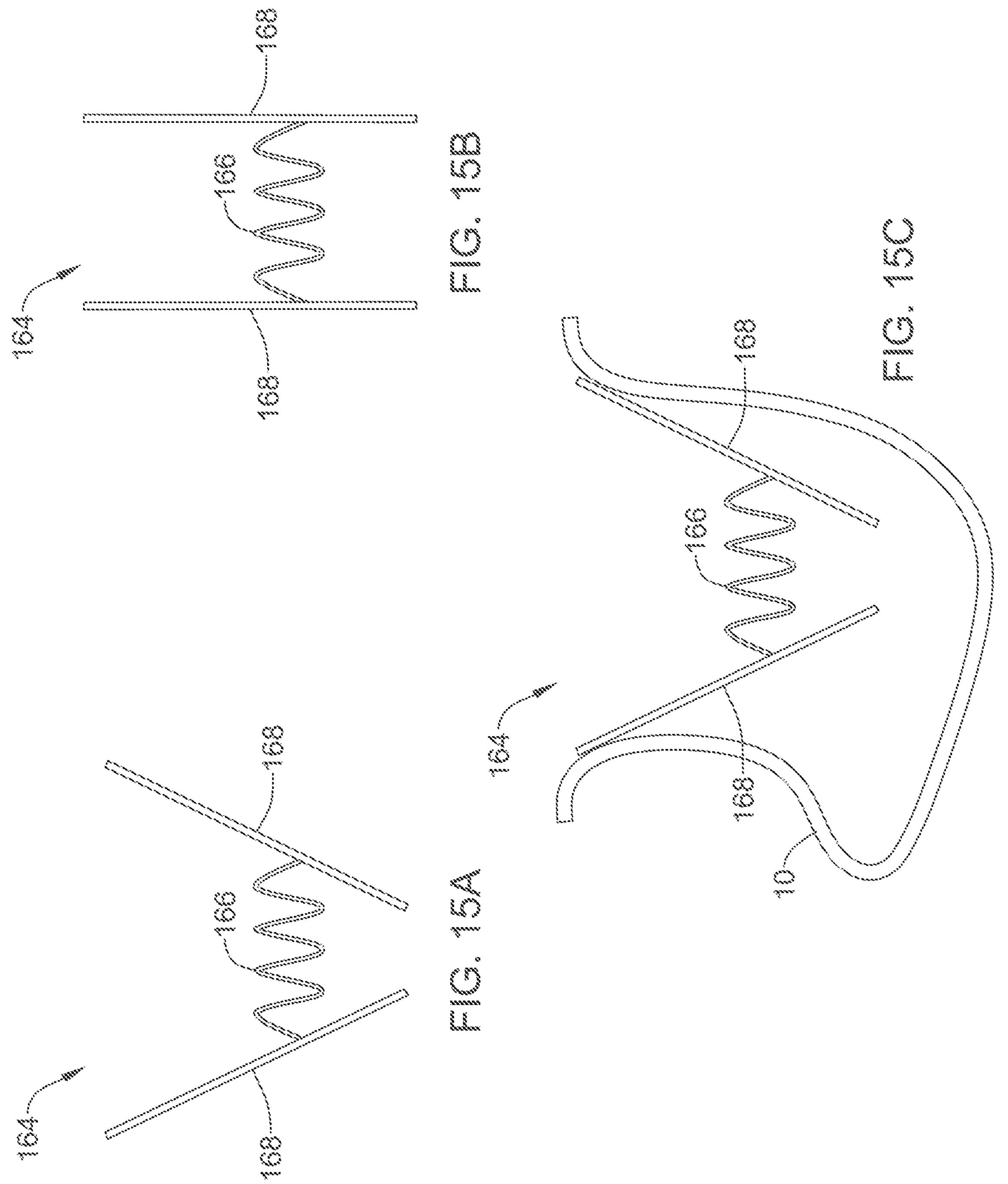
FIGS. 15A, 15B and 15C are schematic views of an illustrative expandable frame usable in an LAAC device.

FIGS. 15A, 15B and 15C are schematic views of an illustrative expandable frame 164 that includes a pivot base 166 and several frame members 168 extending from the pivot base 166. The pivot base 166 may be considered as being an example of the collapsing pivot base 134 (FIG. 10B). In FIG. 15A, the expandable frame 164 is shown in its remembered shape, or expanded configuration, which is the shape that the expandable frame 164 will return to absent any constraining forces. FIG. 15B shows the expandable frame 164 in a collapsed configuration. FIG. 15C shows the expandable frame 164 deployed within the LAA 10. The expandable frame 164 has partially regained its expanded configuration, due to some constraints provided on the expandable frame 166 by virtue of the frame members 168 having contacted anatomy within the LAA 10.

The devices described herein, as well as various components thereof, may be manufactured according to essentially any suitable manufacturing technique including molding, casting, mechanical working, and the like, or any other suitable technique. Furthermore, the various structures may include materials commonly associated with medical devices such as metals, metal alloys, polymers, metal-polymer composites, ceramics, combinations thereof, and the like, or any other suitable material. These materials may include transparent or translucent materials to aid in visualization during the procedure. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In some embodiments, the system and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the system and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An implantable medical device, comprising:

an expandable frame defining a profile of the implantable medical device, the expandable frame moveable between a collapsed configuration for delivery and an expanded configuration for deployment, the expandable frame biased into the expanded configuration, the expandable frame comprising:

a plurality of frame members each having a proximal end and a distal end; and a securement member adapted to secure the plurality of frame members at a location between the proximal end and the distal end of each frame member, the securement member adapted to allow the expandable frame to move between the collapsed configuration and the expanded configuration; and a biasing member that is adapted to bias the expandable frame into the expanded configuration, the biasing member comprising a threaded screw and tether arrangement; and a covering extending over the proximal end of at least some of the plurality of frame members;

wherein each frame member extends linearly from the securement member to the proximal end in the collapsed configuration, and each frame member extends linearly from the securement member to the distal end in the collapsed configuration.

2. The implantable medical device of claim 1, wherein at least some of the plurality of frame members are adapted to bend relative to the securement member when moving between the collapsed configuration and the expanded configuration.

3. The implantable medical device of claim 1, wherein at least some of the plurality of frame members are adapted to pivot relative to the securement member when moving between the collapsed configuration and the expanded configuration.

4. The implantable medical device of claim 1, wherein the plurality of frame members comprise:

a plurality of sealing frame members over which the covering extends; and a plurality of anchoring frame members that are adapted to anchor the implantable medical device in place.

5. The implantable medical device of claim 4, wherein the plurality of sealing frame members pivot in a first direction when moving from the collapsed configuration to the expanded configuration and the plurality of anchoring frame members pivot in a second direction opposite the first direction when moving from the collapsed configuration to the expanded configuration.

6. The implantable medical device of claim 4, wherein the plurality of anchoring frame members comprise anchor hooks extending from a distal end of at least some of the plurality of anchoring frame members.

7. The implantable medical device of claim 1, wherein the expandable frame is biased into the expanded configuration by at least some of the frame members having a remembered shape.

8. The implantable medical device of claim 1, comprising an LAAC (left atrial appendage closure) device.

9. A left atrial appendage closure (LAAC) device, comprising:

an expandable frame moveable between a collapsed configuration for delivery and an expanded configuration for deployment, the expandable frame comprising:

a plurality of frame members each having a proximal end and a distal end, wherein each frame member is substantially straight from the proximal end to the distal end in the collapsed configuration and in the expanded configuration;

a securement member adapted to secure the plurality of frame members, the securement member adapted to allow the expandable frame to move between the collapsed configuration and the expanded configuration; and a biasing member that is adapted to move the expandable frame into the expanded configuration when not otherwise constrained, the biasing member comprising a threaded screw and tether arrangement; and a covering extending over the proximal end of at least some of the plurality of frame members.

10. The LAAC device of claim 9, wherein at least some of the plurality of frame members are adapted to pivot relative to the securement member in response to a biasing force applied by the biasing member.

11. The LAAC device of claim 9, wherein the plurality of frame members comprise:

a plurality of sealing frame members over which the covering extends; and a plurality of anchoring frame members that are adapted to anchor the implantable medical device in place.

12. The implantable medical device of claim 11, wherein the plurality of sealing frame members are adapted to pivot in a first direction and the plurality of anchoring frame members are adapted to pivot in a second direction opposite the first direction when moving from the collapsed configuration to the expanded configuration.

13. A left atrial appendage closure (LAAC) device, comprising:

an expandable frame moveable between a collapsed configuration for delivery and an expanded configuration for deployment, the expandable frame including a plurality of frame members each having a proximal end and a distal end disposed on opposite sides of a securement member secured to each frame member of the plurality of frame members, each of the plurality of frame members adapted to be biased to the expanded configuration when not otherwise constrained; and a covering extending over the proximal end of at least some of the plurality of frame members;

wherein in the expanded configuration, the proximal end of each frame member is disposed radially outward of the securement member and the distal end of each frame member is disposed radially inward of the securement member.

14. The LAAC device of claim 13, wherein the expandable frame comprises a shape memory material.

* * * * *